United States Patent [19]

Bailey

[11] Patent Number: 5,800,179

[45] Date of Patent: Sep. 1, 1998

[54] SYSTEM FOR TRAINING PERSONS TO PERFORM MINIMALLY INVASIVE SURGICAL PROCEDURES

[75] Inventor: Bradford E. Bailey, Brighton, Colo.

[73] Assignee: Medical Simulation Corporation, Houston, Tex.

[21] Appl. No.: 681,455

[22] Filed: Jul. 23, 1996

[51] Int. Cl.$^6$ .................................................. G09B 23/28
[52] U.S. Cl. ........................... 434/262; 434/267; 434/272
[58] Field of Search .............................. 318/568.16, 628, 318/568.11, 568.1; 364/174, 188, 190, 223.3, 224.5, 226.2, 559, 801, 578; 901/9; 395/99; 434/262, 267, 272

[56] References Cited

U.S. PATENT DOCUMENTS

| | | | |
|---|---|---|---|
| 4,205,224 | 5/1980 | Mecklenbord . | |
| 4,360,345 | 11/1982 | Hon . | |
| 4,555,960 | 12/1985 | King | 74/471 X |
| 4,604,016 | 8/1986 | Joyce | 414/7 |
| 4,642,055 | 2/1987 | Saliterman | 434/268 |
| 4,907,973 | 3/1990 | Hon . | |
| 4,950,116 | 8/1990 | Nishida | 414/5 |
| 4,952,024 | 8/1990 | Gale . | |
| 4,954,970 | 9/1990 | Walker et al. . | |
| 4,970,666 | 11/1990 | Welsh et al. . | |
| 4,975,770 | 12/1990 | Troxell . | |
| 5,012,342 | 4/1991 | Olsen et al. . | |
| 5,086,401 | 2/1992 | Glassman et al. | 395/94 |
| 5,113,177 | 5/1992 | Cohen . | |
| 5,116,180 | 5/1992 | Fung et al. | 414/5 |
| 5,193,963 | 3/1993 | McAffee et al. | 414/5 |
| 5,389,865 | 2/1995 | Jacobus et al. | 318/568.11 |
| 5,394,517 | 2/1995 | Kalawsky . | |
| 5,459,382 | 10/1995 | Jacobus et al. | 318/568.11 |
| 5,553,198 | 9/1996 | Wang et al. | 395/80 |
| 5,576,727 | 11/1996 | Rosenberg et al. | 345/179 |
| 5,587,937 | 12/1996 | Massie et al. | 364/578 |
| 5,625,576 | 4/1997 | Massie et al. | 364/578 |
| 5,629,594 | 5/1997 | Jacobus et al. | 318/568.11 |

FOREIGN PATENT DOCUMENTS

95/02233  1/1995  WIPO .

*Primary Examiner*—Richard J. Apley
*Assistant Examiner*—John Rovnak
*Attorney, Agent, or Firm*—Dorr, Carson, Sloan & Birney, P.C.

[57] ABSTRACT

A system for producing highly realistic, real-time simulated operating conditions for interactive training of persons to perform minimally invasive surgical procedures involving implements that are inserted and manipulated through small incisions in the patient. The virtual environment for this training system includes a housing with a small opening. An implement simulating a surgical implement is inserted into the opening and manipulated relative to the housing. A movement guide and sensor assembly monitors the location of the implement relative to the housing and provides data about the implement's location and orientation within the housing. The reported data is interpolated by a computer processor, which utilizes a database of information representing a patient's internal landscape to create a computer model of the internal landscape of the patient. With reference to this computer model, the processor controls the occurrence of force feedback opposing the motion of the implement. A two-dimensional image representing the implement as it would appear within the patient is generated by a processor-controlled video imaging system based on the computer model of the patient's internal landscape. This computer image of the implement is then merged with a video image loop of a patient's internal landscape as it appears through a heartbeat and breathing cycle, and the merged image is displayed on a video display. The combined elements of real-time visual representation and interactive tactile force feedback provide a virtual training simulation with all elements of actual operation conditions, minus a live patient.

5 Claims, 6 Drawing Sheets

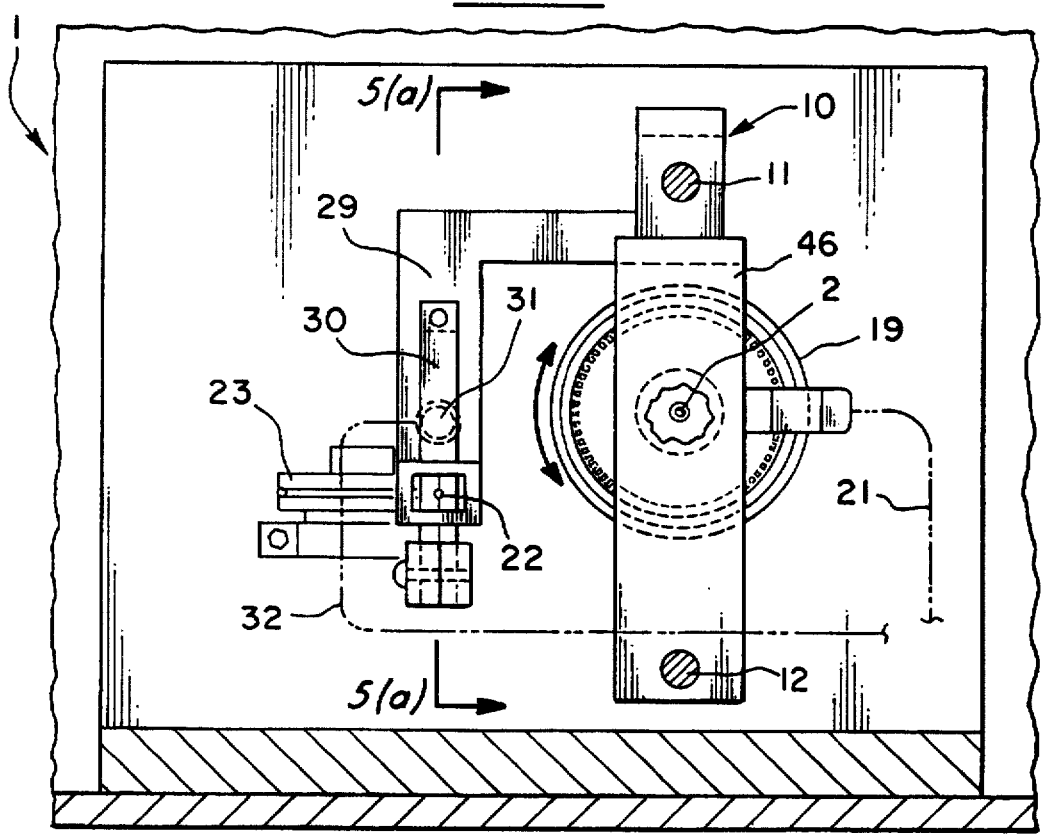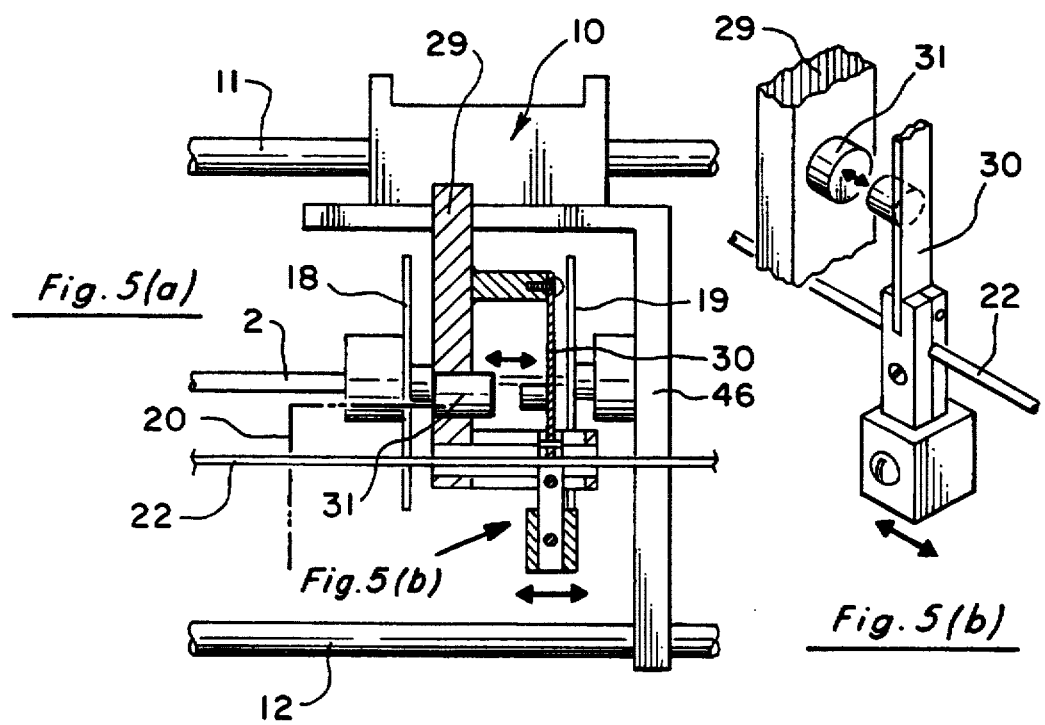

SYSTEM FOR TRAINING PERSONS TO PERFORM MINIMALLY INVASIVE SURGICAL PROCEDURES

BACKGROUND OF THE INVENTION

1. Field of the Invention

The present invention relates generally to the field of simulations for medical training. More specifically, the present invention discloses a system for training persons to perform minimally invasive surgical procedures.

2. Statement of the Problem

Surgery of any form is a stressful imposition on a body. With traditional surgery techniques the incision itself imposes additional risk of infection, trauma, and recovery time upon a patient, beyond that imposed by the condition giving rise to need for surgery. Advances in miniaturization of tools and implements, as well as video systems to view the internal landscapes of patients, have given rise to minimally invasive surgical techniques. In this field of surgery, a tiny incision is made in the patient and the surgical implement is inserted into a vein, artery, or space between tissue. Tactile sensation imparted to the surgeon by the implement as it is inserted into the patient and visual display images from x-ray or other systems allowing an internal view of the body are then used to position the implement and complete the necessary task of the operation, be it repair of an organ such as the heart, removal of blocking tissue, the placement of a pacemaker lead, endoscopic surgery or other procedure. Due to the minimally invasive nature of this type of surgery, operations may be performed in a very brief period of time on patients with less than full anesthesia and hospitalization. Given the nature of this type of operating procedure there are a number of special considerations. Failure to properly orient the implement within the patient, or properly recognize the tissue through which the implement is passing, may result in the implement puncturing or rupturing a vein, artery, organ, or other internal tissue structure. Such an accident will almost certainly result in subjecting the patient to immediate emergency invasive surgery, morbidity, and perhaps mortality. To avoid such an accident, the surgeon must properly associate tactile feedback from the implement and imagery from the display showing the location of the implement relative to the patient's internal landscape. As normal pressures in arteries, tracts, veins, and organs as well as the physical movement of breathing and heartbeat cause changes to the internal patient landscape and affect the movement of the implement, it has seemed that the only way for a practitioner to gain the requisite skills and techniques is by experience with live patients. In addition, the internal conditions and landscapes vary from person to person. For example, constrictions and restrictions appear with sufficient regularity to be expected, but precise locations vary with each patient. Accordingly, the tendency is for those physicians already experienced with the procedure to be asked to perform the operation. It is therefore difficult for inexperienced physicians to obtain a desired level of familiarity and competence leading to requisite certifications. Additionally, there are procedures that are performed on less than a constant basis. Without performing the procedure often, the practitioner has no method to maintain the high degree of skill that is obtained only through routine frequent performance. Further, it is not possible to implement new methods, operations, and procedures except on live persons. Accordingly, there is a need for an effective means to simulate real-life operations, provide tactile force feedback and simulate video imagery of the patient's internal landscape and the surgical implement as they would appear and move in an actual operation, so as to develop and maintain skill, and implement new techniques.

The components involved in the present invention are in some respects similar to video simulation systems, medical training systems, and minimally invasive surgical training systems that have been developed in the past, including the following:

| Inventor | Patent No. | Issue Date |
|---|---|---|
| Kalawsky | 5,394,517 | February 28, 1995 |
| Cohen | 5,113,177 | May 12, 1992 |
| Olsen et al. | 5,012,342 | April 30, 1991 |
| Troxell | 4,975,770 | December 4, 1990 |
| Welsh et al. | 4,970,666 | November 13, 1990 |
| Walker et al. | 4,954,970 | September 4, 1990 |
| Gale | 4,952,024 | August 28, 1990 |
| Mecklenborg | 4,205,224 | May 27, 1980 |
| Hon | 4,907,973 | March 13, 1990 |
| Hon | 4,360,345 | November 23, 1982 |

Kalawsky discloses a computer-controlled integrated real and virtual environment display system having two video cameras matching the simulator user's field of view. Signals from the video cameras are analyzed to determine the presence of predetermined color or intensity. A computer-generated image is then created and positioned within the field of view on the basis of what is or is not perceived to be present in the field of view.

Cohen discloses an apparatus for a display system enabling a pilot in an aircraft to view simultaneously an image of selected display information and a scene external to the aircraft during low visibility conditions. A combined image of the exterior view and display is presented on the pilot's visor.

Olsen et al. disclose a video prioritizer and mixer allowing two or more video sources, such as an in-house data terminal source and a graphics source, to be mixed for display on a single video monitor display.

Troxell discloses a method for enhancing golf green contours for television broadcasts. A grid pattern of intersecting parallel lines is projected over the golf green, recorded, and then broadcast onto a television screen simultaneously with the broadcast of the golf green during play thereon.

Welsh et al. disclose a computerized system for producing highly realistic video images that depict the appearance of a simulated structure in an actual environment, providing for accurate placement and perspective of the structure, allowing renderings of buildings to be viewed in proposed settings prior to actual construction. Measurement of the actual scene is required from the center of view and the camera station point so as to adjust the computer-generated image proportionately.

Walker et al. disclose a system for rapidly generating overlay images by color painting techniques using a host computer with an appropriate graphics-generation operator interface, and for manipulating overlay images with respect to a background image.

Gale discloses a three-dimensional sight and sound reproduction apparatus for individual use. A headset provides visual displays directly before the user's eyes and audio speakers provide sound directly to the user's ears, rendering a user immersed in a three-dimensional virtual reality of sight and sound for enhanced reality and viewing pleasure.

Mecklenborg discloses a binocular viewing technique allowing simulation of objects in close proximity to a flight simulator pilot to be perceived with an enhanced three-dimensional appearance. The images presented to the training individual's left and right eyes are separate and distinct images from respective left and right display systems, which allows the size, shape, and orientation of each image to be separately controlled.

The Hon '345 patent discloses a computer-controlled interactive instruction system for teaching an individual how to administer cardiopulmonary resuscitation. Structured toward comparing a technique being administered to a dummy with standard indicia stored in the computer memory, this system does not propose operator-defined surrogate invasive travel within the subject. Further, this prior art, being structured to specific performances and external responses, does not provide for complete and non-restricted environmental modeling of potentially encounterable conditions.

The Hon '973 patent discloses a computer-controlled interactive instruction system for teaching an individual to perform many types of invasive or semi-invasive procedures. This system incorporates the use of a simulated implement, and a physical model representing, physically and spatially, at least that portion of a patient on which a selected procedure is to be performed. This model is equipped with spaced sensors, constrictors, and other physical characteristics that are used to re-create the physical characteristics of a patient's internal landscape.

3. Solution to the Problem

None of the prior art references uncovered in the search show a minimally invasive surgical procedure simulator having the structure of the present invention. In particular, the system can be used to control tactile force feedback at any point in the procedure, and dynamically adapt the simulation such that the practicing physician does not become accustomed to encountering the same conditions in the same locations, as would never occur in a real operation. Further, none of the prior art cited above incorporates the realism of both visually displaying and tactilely affecting the implement within the patient as the patient's internal landscape is continually changed by the process of breathing and heartbeat.

SUMMARY OF THE INVENTION

A system is disclosed for producing highly realistic, real-time simulated operating conditions for interactive training of persons to perform minimally invasive surgical procedures involving implements that are inserted and manipulated through small incisions in the patient. The system includes a housing with a small opening. An implement simulating a surgical implement is inserted into the opening and manipulated relative to the housing. A movement guide and sensor array assembly monitors the location of the implement relative to the housing and provides specific data of the implement's location and orientation within the housing. Additionally, the movement guide and sensor array assembly monitors the force applied to the implement by the training person throughout the duration of the training simulation. Utilizing a database of information representing a patient's internal landscape and data driven software, a computer processor creates a computer model of the internal landscape of the patient. Data regarding the implement's location and orientation is interpolated by the processor with reference to this computer model of the patient's internal landscape. With reference to this computer model, the processor controls the occurrence of force feedback opposing the motion of the implement. Further, a two-dimensional image representing the implement as it would appear within the patient is generated by a video imaging system based on the computer model of the patient's internal landscape. This computer image of the implement is then merged with a video image loop of a live patient's internal landscape as it appears through a synchronized heartbeat and breathing cycle. The merged images are then displayed on a video display.

A first object of the present invention is to provide a realistic minimally invasive surgical simulation of operating conditions, inclusive of tactile force feedback at any point of implement insertion, thus allowing the simulation to more realistically approximate surgical conditions in a real patient.

Another object of the present invention is to provide a highly realistic visual depiction of the operating procedure as it would appear in actual operating conditions, with specific attention to the changes of the patient's internal landscape and implement location as occur with the natural process of the patient's heartbeat and breathing.

Yet another object of the present invention is to provide a minimally invasive surgical simulation that can be easily modified to simulate different patients or operating procedures without the necessity of physically modifying or adjusting the physical movement guide and sensor assembly.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 4 is an end cross-sectional view of the movement guide and sensor assembly 10 within the housing 1 and connected to the implement 2.

FIG. 5(a) is a partial side view of the movement guide and sensor assembly 10, depicting the connection of the framed assembly 46 component of the movement guide and sensor assembly 10 to a guide cable 22 used to create force feedback to the implement 2.

FIG. 5(b) is a partial side view of the movement guide and sensor assembly 10, providing an enlarged view of the framed assembly 46 connection to the guide cable, depicting the sensor measuring the relative force applied to the implement.

DETAILED DESCRIPTION OF THE INVENTION

Figure 1:
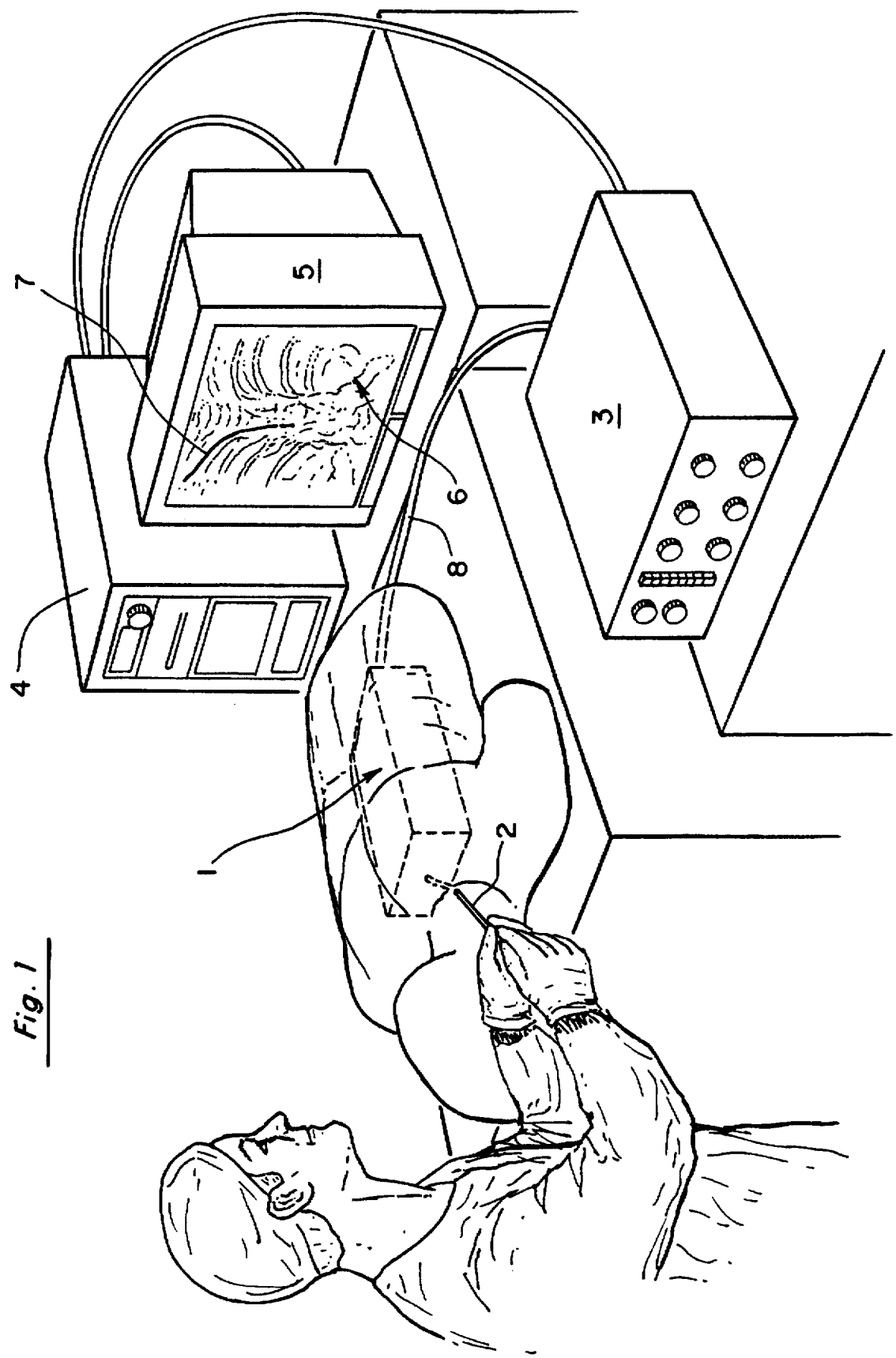
FIG. 1 is a simplified diagram providing an overview of the present system including an implement, sensor assembly, processor, and video display to create a realistic tactile and visual environment for training of a minimally invasive surgical procedure.

Turning to FIG. 1, the system for training persons to perform minimally invasive surgical procedures includes a housing 1, containing the movement guide and sensor assembly (described below), an implement 2 for simulating a surgical implement used in minimally invasive surgical procedures, a processor 3 for interpreting the data from the sensor, a computer 4 containing a video processor, and a display 5 for providing a visual display of the patient's internal landscape 6 with a computer-generated two-dimensional image 7 of the implement 2 as it is inserted and manipulated through the procedure. Although depicted in FIG. 1 as separate, the processor 3 may well be reduced to a single computer interface card that is placed directly within the computer 4. In either case the sensors within the housing 4 are connected to the processor 3 by standard wiring 8. It is to be understood that the implement 2 as employed in the present invention may be a simulation equivalent to a catheter, endoscope, arthroscope, pacemaker lead implant, or other commonly used minimally invasive tool or device. The computer 4 is understood to be of a conventional Pentium processor type with conventional memory and storage means. The display 5 is understood to be a conventional video monitor type and may be NTSC, PAL, VGA, or SVGA.

Figure 2:
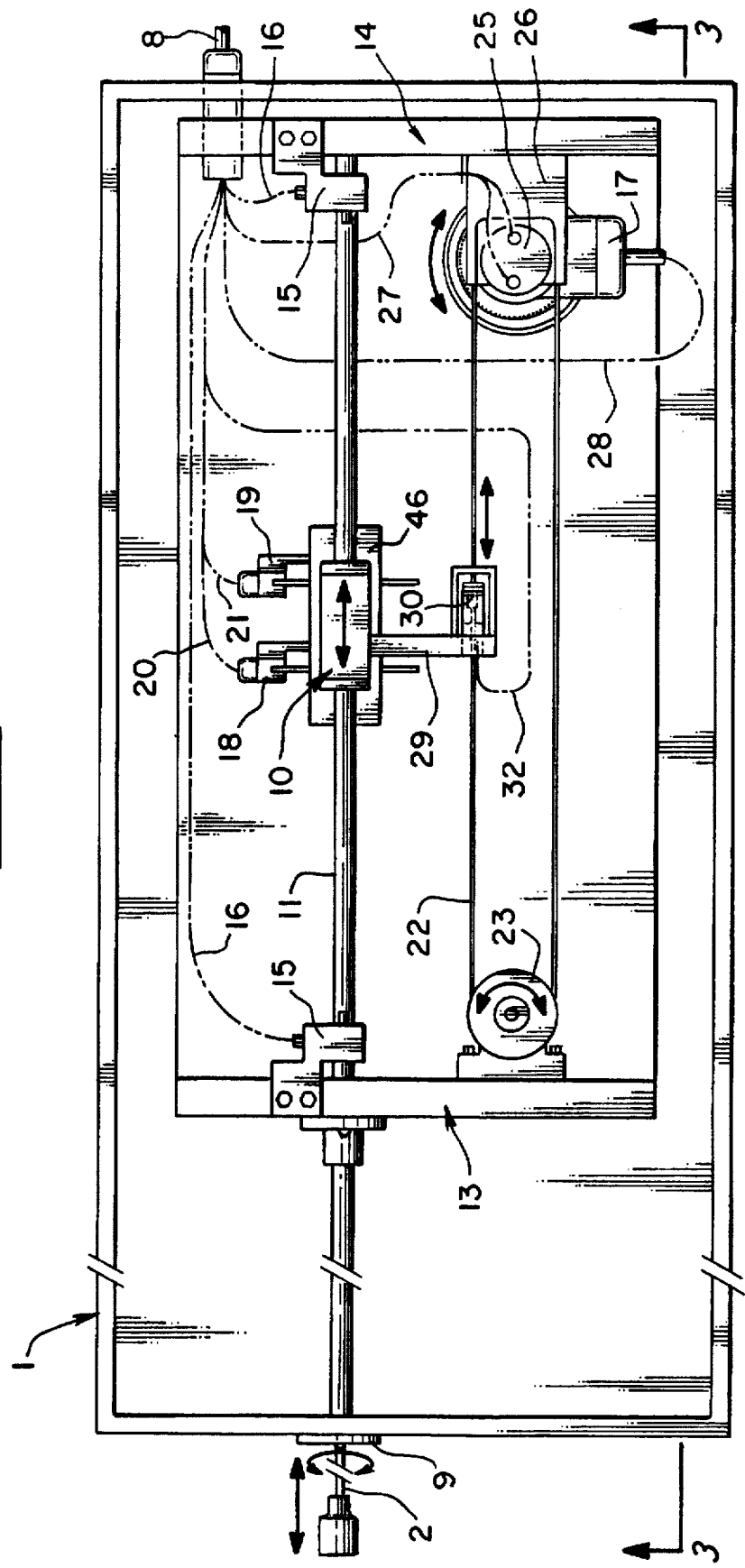
FIG. 2 is a top cross-sectional view of the movement guide and sensor assembly 10 within the housing 1 and connected to the implement 2.
Figure 3:
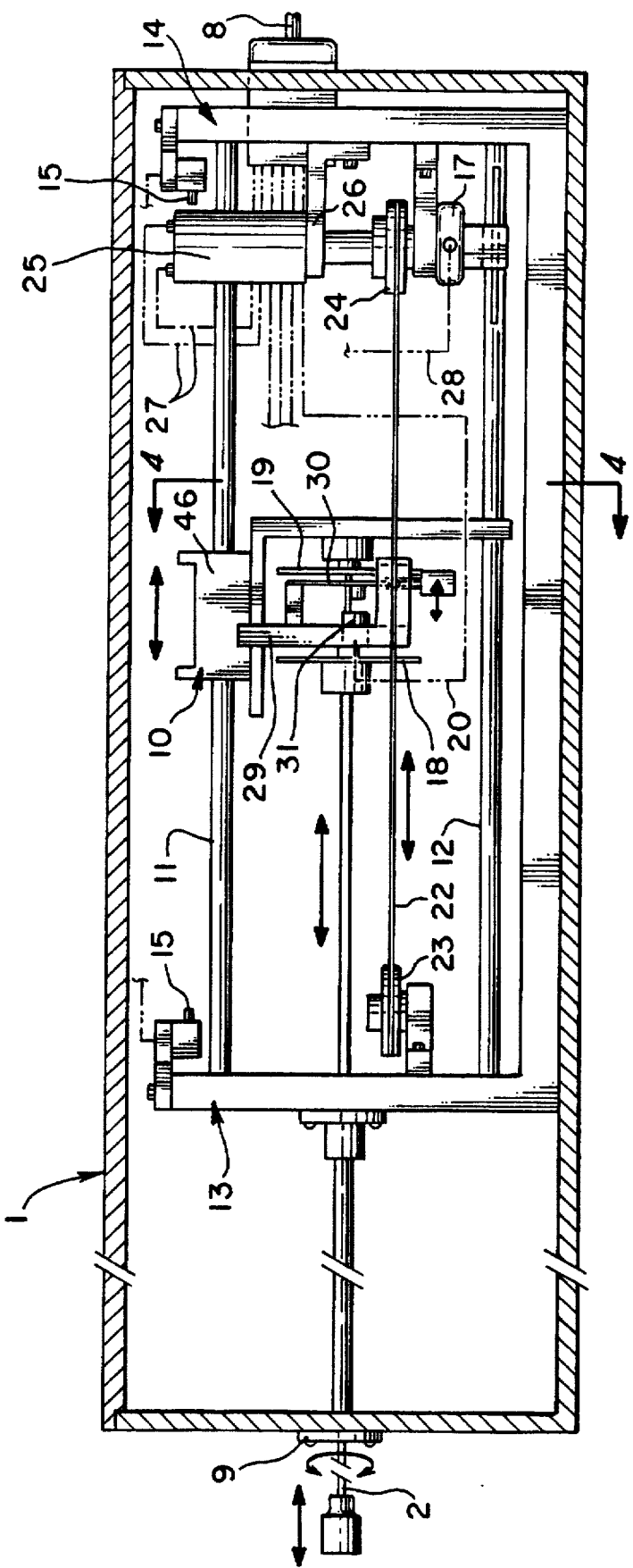
FIG. 3 is a side cross-sectional view of the movement guide and sensor 10 assembly within the housing 2 and connected to the implement 2.

In FIGS. 2 and 3, the configuration of the movement guide and sensor 10 within the housing 1 is depicted as seen from the top (FIG. 2) and from the side (FIG. 3). The implement 2 is inserted through an opening 9 in the housing 1. Simulating a true minimally invasive surgical instrument, the implement 2 may be moved axially (or laterally) and rotationally relative to the housing 1. Inner components of the implement 2 may also be rotated independently from the implement 2 as a whole. The distal end of the implement 2 within the housing 1 is affixed to a movement guide and sensor assembly 10 (see FIGS. 2 and 3). This movement guide and sensor assembly 10 serves to restrict the motion of the implement 2 within the housing 1, and provide accurate sensing of the implement 2 relative to the housing 1.

In the present invention this is accomplished by using a framed assembly 46, to which rotation sensors 18 and 19, a leaf spring 30, applied force sensor 31, and attachment arm 29 are affixed (each of these components is further discussed below). The framed assembly 46 is in turn mounted on parallel guide rails 11 and 12, and connected to a guide wire 22 as shown in FIG. 3. The guide rails 11 and 12 are supported by two parallel surfaces 13 and 14 attached in an orientation perpendicular to the base of the housing 1. Collectively, the framed assembly 46 with components described above, guide wire 22, and the guide rails 11 and 12 form the movement guide and sensor assembly 10.

The nature and design of the implement 2 is such that it is flexible so as to easily bend and conform to the artery, vein, or other internal space through which it is being inserted in a real patient. For purposes of simulating the operating procedure with the present invention, it is necessary only to know the precise depth of insertion as well as the orientation of the implement 2. For this purpose, in the preferred embodiment, all linear movement of the implement 2 is confined to a single axis within the housing 1. This limitation in axial motion further serves to reduce friction affecting the movement of the implement by minimizing the movement control components. Limit switches 15 are placed at either end of the guide rail 11, and are used to reset the position of the movement guide and sensor assembly 10 prior to the start of each operation simulation. The limit switches 15 are connected to the processor 3 by wires 16. Alternatively, one or both of the limit switches 15 may be affixed to the moving movement guide and sensor assembly 10. The zero setting calibration may also be achieved with the movement position sensor 17.

Rotation of the implement 2 or of the internal components of the implement 2 is reported by axial rotation sensors 18 and 19 proximately located to the distal end of the implement 2 and affixed to the framed assembly 46. In the preferred embodiment as depicted, these rotation sensors 18 and 19, as well as the movement position sensor 17, are conventional optical sensor assemblies. However, it is to be understood that potentiometers, magnetic sensors, and other conventional rotation sensors may be substituted. The rotation sensors 18 and 19 are connected to the processor 3 by wires 20 and 21. All wires passing from the housing 1 to the processing unit 3 are bundled into common wire 8 shown in FIG. 1.

In the preferred embodiment as depicted in FIGS. 2 and 3, a guide cable 22 is positioned relative to the guide rails 11 and 12 and to the mounted framed assembly 46. The guide cable 22 travels about a freewheeling pulley 23 and about a pulley 24 affixed to a servo motor 25 and movement sensor 17, forming a combined pulley-servo-sensor unit 26. As the purpose of the servo motor is to apply resistive torque force to the guide cable (as more fully described below), it is understood that a stepper motor, variable clutch system, or other motion retarding system could be employed. As depicted in FIGS. 2 and 3, a pulley 23 is affixed to the perpendicular support surface 13 and the pulley-servo-sensor unit 26 is affixed to the perpendicular support surface so as to achieve horizontal placement of the guide cable 22 proximate to the framed assembly 46 component of the movement guide and sensor assembly 10. In the alternative, the pulley 24 could be affixed to support surface 14 and the pulley-servo-sensor unit 26 affixed to support surface 13, without effect to the present invention. The servo motor 25 is controlled by the processor 3 through wires 27. The movement sensor 17 is connected to the processor 3 by wires 28.

The movement guide and sensor assembly 10 is affixed to the guide cable 22 by means of an attachment arm 29 and leaf spring 30 (see FIGS. 4, 5(a), and 5(b)). Axial motion of the implement 2 imparts motion to the framed assembly 46 portion of the movement guide and sensor assembly 10, which in turn via the attachment arm 29 and leaf spring 30 imparts motion to the guide cable 22 and rotation of the pulley-servo-sensor unit 26. Force feedback to the implement 2 is achieved by applying a counter torsional force to the rotation of the pulley-servo-sensor unit 26. With the servo motor 25 engaged to apply the torsional force preventing movement, motion of the framed assembly 46 portion of the movement guide and sensor assembly 10 relative to the stationary guide cable 22 results in a deflection of the leaf spring 30. The deflection of the leaf spring 30 is sensed by an applied force sensor 31 (see FIGS. 5 and 5(a)). The attachment of the applied force sensor 31 to the traveling framed assembly 46 allows force feedback to be imparted to the implement 2 at any time or location during axial motion of the implement 2, and as often as is desired for the simulation. Additionally, the dynamic positioning of the applied force sensor 31, as induced by the motion of the movement guide and sensor assembly 10, allows the simulation to be changed without requiring physical adjustment to the location of the applied force sensor 31 or the force feedback-inducing pulley-servo-sensor unit 26.

In FIGS. 4, 5(a), and 5(b), a more detailed cross section of the movement guide and sensor assembly is depicted. The rotation sensors 18 and 19 are positioned within the framed assembly 46, and proximate to the implement 2. The attachment arm 29, leaf spring 30 and guide cable 22 appear as positioned in the current preferred embodiment. A change in location, orientation, or means of connection between the movement guide and sensor assembly 10 and guide cable 22 does not alter the performance of the present invention. Additional rotation sensors or motion sensors could be included. In particular additional sensors can be used to monitor the location and rotation of individual components within the implement assembly (e.g. with operation simulations involving the clearing of blocked passage passageways within the body the simulation implement will contain a drill or stylus component). It is understood that the inclusion of additional rotation sensors and, or additional movement guide and sensor assemblies for additional simulated implements, or implement internal components does not change the operation of the present invention, but rather are intended variations of the present invention to accommodate advanced simulations.

In FIGS. 5(a) and 5(b), the leaf spring 30 and applied force sensor 31 of the preferred embodiment are depicted. There are many current methods of detecting applied force, and use of a leaf spring 30 and an applied force sensor 31 in the form of a magnetic sensor as depicted in the current embodiment are not intended to exclude alternative applied force sensing means. The applied force sensor 31 is connected to the processor 3 by wire 32.

Figures 6A, 6B, 6C:
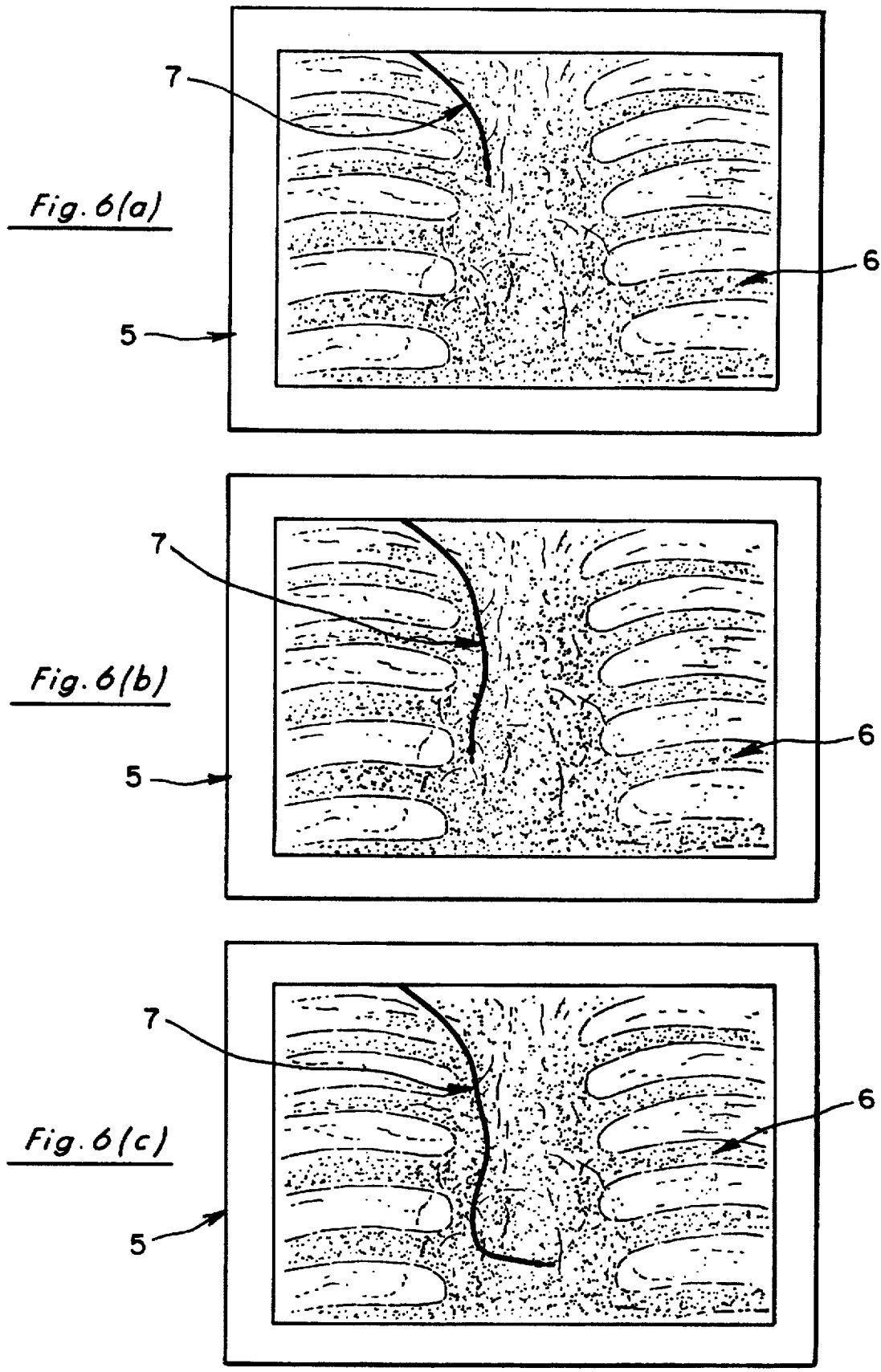
FIGS. 6(a), 6(b), and 6(c) are display images depicting the merged image of the computer-generated implement and the real video of a patient's internal landscape as the implement is moved during the operation procedure.

In FIGS. 6(a), 6(b), and 6(c), the merged image of actual video of the internal landscape 6 of a patient and the computer-generated two-dimensional image 7 of the implement 2 as it is manipulated through a simulation is depicted upon a display 5. To create a computer model of the internal landscape 6 of the patient, actual video of a live patient is used. With a normal patient, the breathing cycle and heartbeat cycle have different rates, giving rise to the usual occurrence of several heartbeats for each breath. Breathing directly affects the size and configuration of a patient's internal landscape in a continuous manner. Likewise, the heartbeat imparts a repetitive effect to the landscape; however, the combined effect is quite variant given where in the breathing cycle the heartbeat occurs.

A video frame depicting the simultaneous start of a breathing cycle and start of a heartbeat is identified from the actual video. Likewise a video frame depicting the simultaneous end of a breathing cycle and end of a heartbeat is identified from the actual video. Depending on the live patient, this second frame of synchronized ending heartbeat and breathing cycle may occur one or more breaths in time after the starting breath. With these identified frames of video it is then possible to create a recurring loop of video by splicing together the synchronized frames.

The video loop thus provides a visual depiction of the internal landscape as it is affected by the normal process of breathing and heartbeat. This video loop is digitized and stored as a computer video file in a conventional storage device within the computer 4.

From this video loop, video images of the patient's internal landscape in its fully expanded and fully contracted states are identified, and the pathways of arteries, veins, and internal structures are identified in accordance with the operation to be simulated. The locations of these internal structures, arteries, and veins are then traced with a computer encoding device such as light pen, plotter, or other device to create a database of boundary point locations for the internal structures. From the boundary points a mathematical algorithm then determines all plot positions for the internal structures within the boundaries, in accordance with the heartbeat and breathing cycles (for example, by linear interpolation, etc.). This data base of boundary and plot position points for the internal structures is then utilized by data driven software and the computer processor 3 to create a working computer model of the patient's internal landscape.

Sensor data from the rotation sensors 18 and 19 and movement position sensor 17 is interpolated by the processor 3, and position coordinates for a computer-generated two-dimensional image of the implement 2 are calculated. The calculated values for this two dimensional image of the implement are then used by the video imaging processor, contained within the computer 4, to create a two-dimensional image 7 of the implement 2. The two-dimensional image 7 of the implement 2 is merged with each frame of the video loop image to depict the internal landscape 6 of the patient. In this manner it is possible to simulate all positions of the internal structures and motion of the implement 2 as the simulated operation is conducted, in the same manner as the internal structures and implement 2 would move in a real patient.

The merged image of the patient's internal landscape 6 and the computer-generated two-dimensional image 7 of the implement 2 is presented to the display 5 in a format consistent with the display characteristics (e.g., NTSC, PAL, VGA or SVGA), as shown in FIGS. 6(a), 6(b), and 6(c). Standard information regarding the patient's vital signs may also be presented on the display 5.

Figure 7:
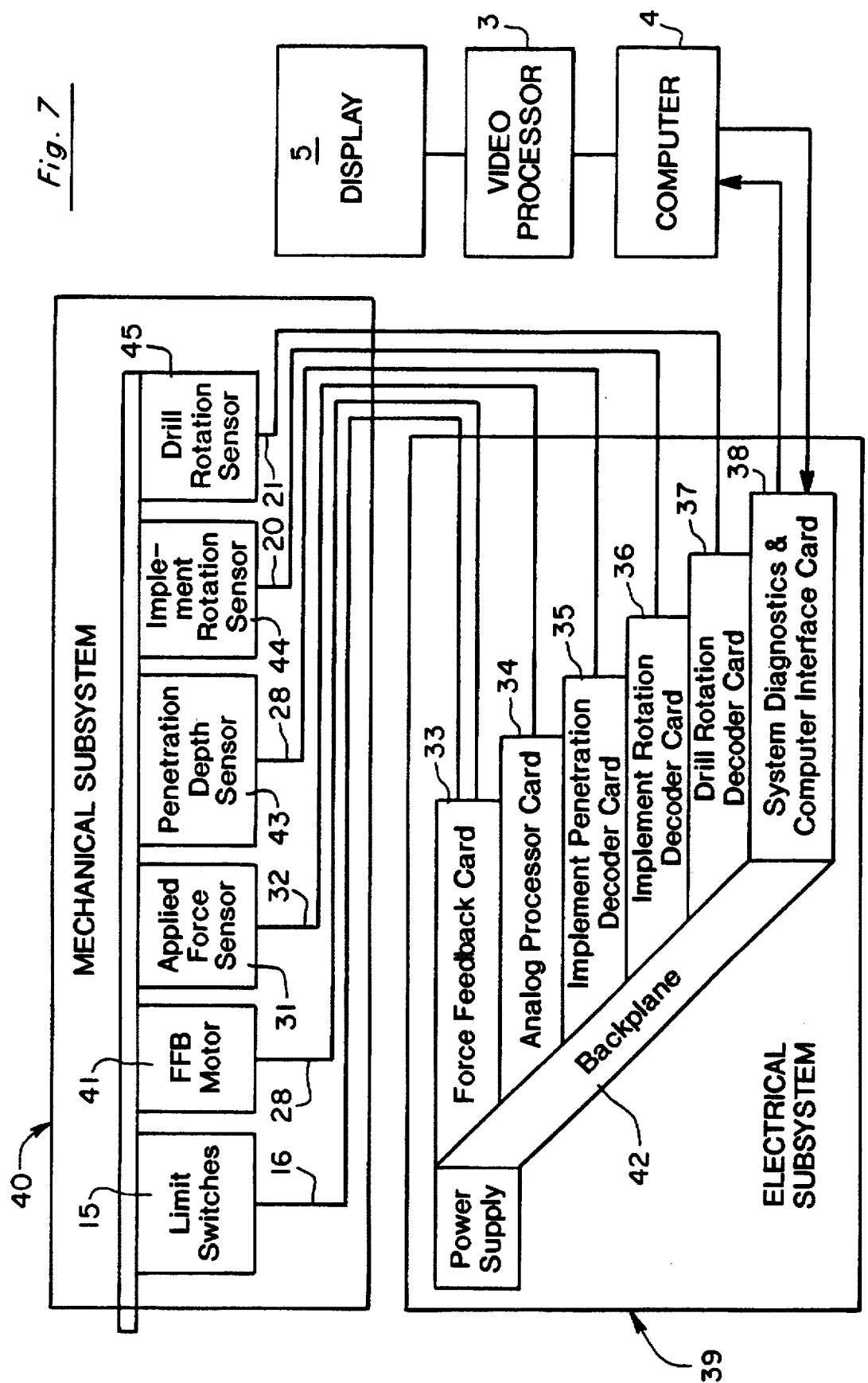
FIG. 7 is a simplified block diagram showing the inter relation of the system components.

In FIG. 7, the interrelationship between system components is set forth. There are two subsystems, an electrical subsystem 39, and a mechanical subsystem 40. Each of the elements depicted in the mechanical subsystem 40 is contained within the housing 1.

Turning to the electrical subsystem 39, the relationship of the sensor receiving components is shown. Depicted as separate components, the force feedback card 33 is used in connection with the limit switches 15 to set a zero axial motion point at the beginning of each simulation and to control the pulley-servo-sensor unit 26 (FIGS. 2 and 3), depicted here as FFB motor 41. The analog processor card 34 is responsible for monitoring the force applied to the implement 2 as reported by the applied force sensor 31 (FIGS. 3, 4, 5(a), and 5(b)). This monitored force is communicated to the force feedback card 33 by the connecting backplane 42. The implement penetration decoder card 35 is responsible for monitoring the axial motion of the implement 2 relative to the housing 1. Identified in FIGS. 2 and 3 as the movement sensor 17, the penetration depth sensor 43 informs the implement penetration decoder card 35 of all axial motion made by the implement 2. This information is communicated to the processor 3 by the connecting backplane 42 and computer interface card 38. The implement rotation decoder card 36 is responsible for monitoring axial rotation of the implement 2 relative to the housing 1, as reported by the rotation sensor 18 in FIGS. 2, 3, 4, and 5(a), which is depicted as the implement rotation sensor 44 in FIG. 7. In certain procedures the implement 2 may contain an internal component such as a stylus, a drill, or both that may be rotated independently from the implement 2 itself. To further application to numerous simulations, the necessary rotation sensor 19 in FIGS. 2, 3, 4, and 5(a), identified as the drill rotation sensor 45 in FIG. 7, is incorporated into the present invention and connected to a drill rotation decoder card 37. The drill rotation sensor 45 functions in a manner similar to that of the implement rotation sensor 44. The drill decoder card 37 functions in a manner similar to that of the implement rotation decoder card 36. The system diagnosis and computer interface card 38 is responsible for correlating all information between the electrical subsystem 39 components, as collected from the mechanical subsystem 40, and interfacing with the processor 3. Although depicted as separate, the components of the electrical subsystem 39 may be combined in one or more logical component and located within either the mechanical subsystem or computer or both. Collectively the components of the electrical subsystem 39 and the mechanical subsystem 40, when connected to the processor 3, allow the processor 3 to control the location and occurrence of tactile force feedback. Alternatively, further reduction in electrical component size will produce an electrical subsystem that may be treated as a simple computer interface board with an on-board processor. Such a board may then be placed within the computer 4, eliminating external space required by the separate electrical subsystem 39.

The above disclosure sets forth a number of embodiments of the present invention. Other arrangements or embodiments, not precisely set forth, could be practiced under the teachings of the present invention and as set forth in the following claims.

We claim:

1. A system for training persons to perform a minimally invasive surgical procedure using a surgical implement that is inserted and manipulated through a small incision in a patient, said system comprising:

a housing with an opening;

an implement for simulating said surgical implement that is manually inserted through said opening in said housing and manipulated axially and rotationally relative to said housing;

a movement guide and sensor assembly for monitoring the position of said implement relative to said housing, said movement guide and sensor assembly having:
   a) a guide cable;
   b) a guide rail proximate to said guide cable;
   c) a framed assembly mounted on said guide rail for restricting the linear motion of said implement as it is moved relative to said housing to a predetermined axis;
   d) a rotation sensor affixed to said implement for monitoring the axial rotation of said implement relative to said housing;
   e) a position sensor on said guide rail for monitoring the axial position of said framed assembly; and
   f) a connection means connecting said guide cable and said framed assembly, such that motion of the framed assembly along the guide rail imparts motion to the guide cable;

a force feedback system for producing an adjustable force opposing the motion of said implement having;
   a) an applied force sensor sensing applied force to said implement; and
   b) a servo motor applying a torque to said guide cable, which by connection of said connection means to said framed assembly attached to said guide rail, imparts a resistive force to linear motion of said implement;

a display;

a video imaging system for producing a video image simulation of said implement superimposed on a visual representation of the patient's internal landscape; and a processor for interpreting the data from said rotation sensor and said position sensor to determine the location and occurrence of force feedback to said implement, said force feedback created by said processor controlling said servo motor in response to said sensed applied force, said processor also controlling said video imaging system to create a visual simulation for said display.

2. The system of claim 1, further comprising means for detecting the amount of axial force applied to said implement by the training person.

3. The system of claim 1, wherein said processor further comprises means for producing a visual display image depicting the patient's internal landscape with a superimposed two-dimensional image of said implement, said display image incorporating the effect of heartbeat and breathing cycle upon the appearance of both said internal landscape and said two-dimensional image of said implement.

4. The system of claim 1 wherein said implement contains internal components which may be independently manipulated, and wherein said movement guide and sensor means further comprises means for sensing axial rotation of said implement's internal components relative to said housing.

5. The system of claim 3 wherein said means for producing a visual image depicting the patient's internal landscape further comprises a computer model having:

a series of video frames showing images of the patient's internal landscape through a breathing and heartbeat cycle;

a first array of points indicating the path for insertion of said implement in the video frame showing the patient's chest fully contracted;

a second array of points indicating the path for insertion of said implement in the video frame showing the patient's chest fully expanded;

means for determining the limits of said implement's pathway and movement within the internal landscape based on said first array of points when fully contracted and said second array of points when fully expanded;

means for creating two-dimensional computer images of said implement in shape and contour as indicated by the sensed position and orientation of said implement in relation to said determined limits of pathway; and means for superimposing said two-dimensional images of said implement on said video frames by interpolating the location of said implement and corresponding video frame of said patient's internal landscape, using said determined limits of pathway.

* * * * *